US010252075B2

(12) United States Patent
Reis et al.

(10) Patent No.: US 10,252,075 B2
(45) Date of Patent: Apr. 9, 2019

(54) OCULAR THERAPY DEVICE

(71) Applicant: TAD BAVARIA GMBH, Diespeck (DE)

(72) Inventors: Werner Reis, München (DE); Ronald Spaltmann, Grassau (DE)

(73) Assignee: TAD BAVARIA GMBH, Diespeck (FR)

( * ) Notice: Subject to any disclaimer, the term of this patent is extended or adjusted under 35 U.S.C. 154(b) by 424 days.

(21) Appl. No.: 14/785,502

(22) PCT Filed: Mar. 21, 2014

(86) PCT No.: PCT/EP2014/000798
§ 371 (c)(1),
(2) Date: Oct. 19, 2015

(87) PCT Pub. No.: WO2014/173485
PCT Pub. Date: Oct. 30, 2014

(65) Prior Publication Data
US 2016/0067521 A1    Mar. 10, 2016

(30) Foreign Application Priority Data

Apr. 23, 2013  (DE) .................. 10 2013 007 074

(51) Int. Cl.
*A61N 5/06* (2006.01)
*A61F 9/007* (2006.01)
(Continued)

(52) U.S. Cl.
CPC .............. *A61N 5/0613* (2013.01); *A61F 9/00* (2013.01); *A61F 9/008* (2013.01); *A61F 9/0079* (2013.01);
(Continued)

(58) Field of Classification Search
CPC ...... A61N 5/06; A61N 5/0613; A61N 5/0618; A61N 5/062; A61N 5/0622;
(Continued)

(56) References Cited

U.S. PATENT DOCUMENTS 5,757,462 A * 5/1998 Nanjo .................... A61B 3/117
                                                        351/206
6,030,376 A * 2/2000 Arashima .............. A61B 3/113
                                                        606/12

(Continued)

FOREIGN PATENT DOCUMENTS

DE   102006030219 A1   1/2008
DE   102010020194 A1   11/2011
EP      2380535 A1   10/2011

OTHER PUBLICATIONS

International Search Report for International Application No. PCT/EP2014/000798 dated Jul. 2, 2014.

*Primary Examiner* — Ahmed Farah
(74) *Attorney, Agent, or Firm* — Fitch, Even, Tabin & Flannery LLP

(57) ABSTRACT

The invention relates to an ocular therapy device having a radiation source emitting UV light and an optical imaging system disposed downstream of the radiation source for imaging a therapy beam coming from the radiation source in an ocular imaging plane, wherein an optical condenser unit is disposed downstream of the radiation source and comprising a diaphragm unit, an optical means for influencing a spatial energy distribution which can be associated with the therapy beam and is oriented along the therapy beam cross-section, and comprising an optical means for influencing a beam form, which can be associated with the therapy beam.

18 Claims, 6 Drawing Sheets

(51) Int. Cl.
*A61F 9/008* (2006.01)
*A61F 9/00* (2006.01)
(52) U.S. Cl.
CPC ............ *A61F 2009/00872* (2013.01); *A61N 2005/0626* (2013.01); *A61N 2005/0643* (2013.01); *A61N 2005/0661* (2013.01)
(58) Field of Classification Search
CPC .... A61N 2005/0632; A61N 2005/0643; A61N 2005/0648; A61N 2005/065; A61N 2005/0651; A61N 2005/0658; A61N 2005/0661; A61N 2005/0664; A61N 2005/066; A61F 9/00; A61F 9/008; A61F 9/0061
USPC ........ 607/88–92, 94; 606/351; 351/204–208, 351/210–212
See application file for complete search history.

(56) References Cited

U.S. PATENT DOCUMENTS

| | | | | |
|---|---|---|---|---|
| 6,245,058 B1* | 6/2001 | Suzuki | .................... | A61F 9/008 219/121.62 |
| 6,508,812 B1* | 1/2003 | Williams | ............ | A61F 9/00806 606/10 |
| 6,585,723 B1* | 7/2003 | Sumiya | .................. | A61B 3/107 606/10 |

* cited by examiner

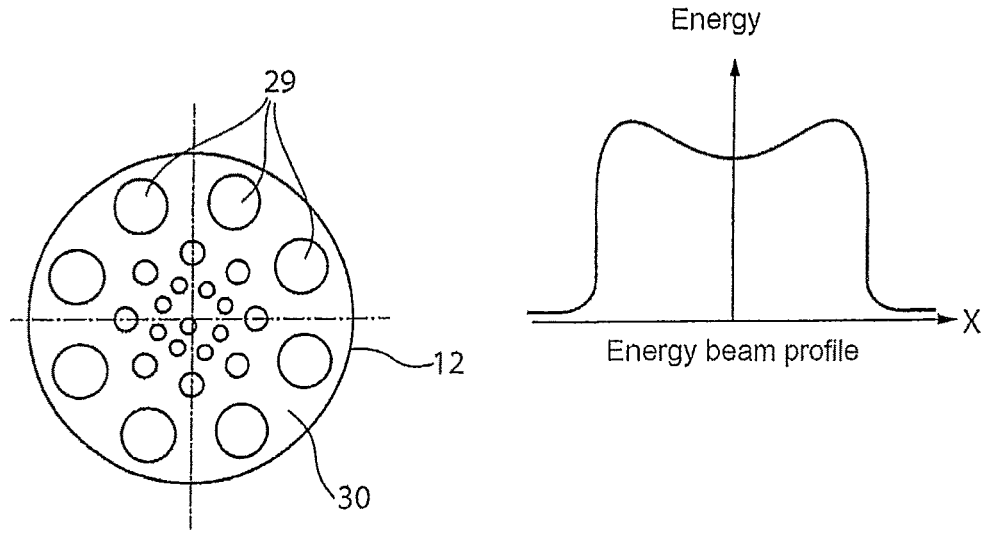
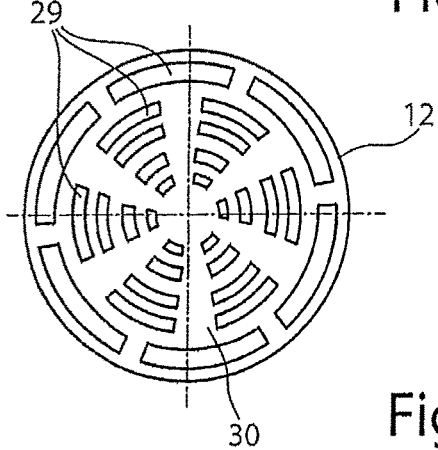
Fig. 3a
Fig. 3b
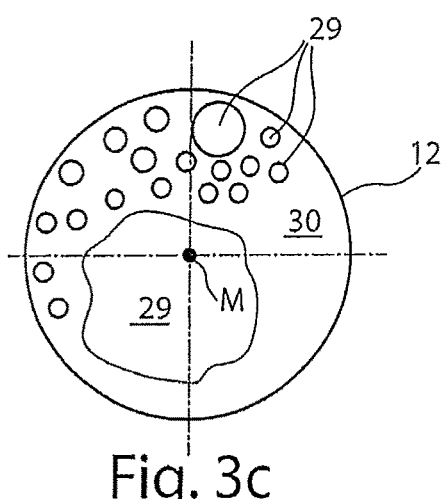
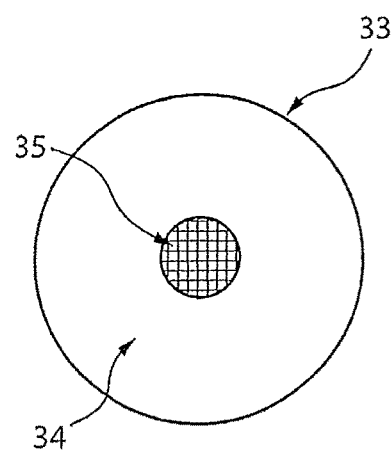
Fig. 3c
Fig. 3d

OCULAR THERAPY DEVICE

CROSS REFERENCE TO RELATED APPLICATIONS

Reference is made to German Patent Application No. 10 2013 007 074.0, filed on Apr. 23, 2013, and International Patent Application No. PCT/2014/000798, filed on Mar. 21, 2014, which applications are incorporated herein by reference in their entirety.

BACKGROUND OF THE INVENTION

Field of the Invention

The invention relates to an ocular therapy device having a source that emits UV light and an optical imaging system located downstream from the radiation source for imaging a therapy beam emitted by the radiation source in an ocular imaging plane, having an optical condenser unit situated downstream from the radiation source, a diaphragm unit, an optical means for influencing a spatial energy distribution that can be assigned to the therapy beam and is oriented along the therapy beam cross section as well as an optical means for influencing a beam shape that can be attributed to the therapy beam.

Description of the Prior Art

DE 10 2006 030 219 A1 describes a generic irradiation system for medical applications in which a photo-induced cross-linking of ocular tissue, i.e., optic tissue, is initiated by means of ultraviolet radiation. In particular in the presence of photosensitizers additionally introduced into the optic tissue to be treated, a local application of UV radiation to the eye to be treated is capable of altering the biomechanical properties of the ocular tissue. Ocular tissue regions, in particular of the external fibrous tunic of the eyeball, in particular the region of the cornea, can be treated with the help of such a photo-induced treatment. Deformations in the external regions, in particular of the external fibrous tunic of the eyeball, in particular the region of the cornea, can be treated. Deformations of the external fibrous tunic of the eyeball, which are caused by diseases or heredity and are usually associated with faulty vision, can typically be treated by photo-induced cross-linking of ocular tissue, especially since the treatment permits a photochemical stabilization, which does not cause tissue ablation and permits a change in the biomechanical or biochemical properties of the cornea.

A generic treatment device typically has a UV radiation source, whose emitted UV radiation is imaged on an ocular imaging plane with the help of an optical system consisting of at least two lenses. The section of the eye to be treated in a patient, for example, the cornea of a patient's eye, is to be positioned in this ocular imaging plane. To influence the beam size and also the energy distribution along the beam cross section of the therapy beam imaged in the ocular imaging plane, a diaphragm, which limits the therapy beam geometrically, as well as an optical element, which influences the energy distribution of the therapy beam and has a diffractive or holographic effect, are introduced along the path of the therapy beam.

EP 2 380 535 A1 describes a device for cross-linking ocular tissue with electromagnetic radiation, in which an optical means for adjusting a heterogeneous distribution of the radiation current density of the therapy beam imaged in the ocular imaging plane is introduced along the path of the therapy beam. In particular, the optical means is capable of adjusting the depth of treatment of the electromagnetic radiation in the desired manner within the ocular tissue to be treated, which is situated in the ocular imaging plane. For example, an absorber plate, through which the therapy beam passes and which has different absorption regions along the cross section of the therapy beam, is suitable for this purpose.

DE 10 2010 020 194 A1 discloses a method and a device for stabilizing the ocular cornea, in which the cornea is irradiated successively and locally in different regions, such that collagen fibers are cross-linked with one another in the irradiated locations. For irradiation in different locations, the therapy beam path is designed optically, so that the laser beam irradiates only a local portion of the cornea at one point in time but not the entire cornea.

Generic treatment devices that are known so far have a complex and usually an expensive equipment setup, which must be adjusted accurately with respect to a spatially fixed patient eye to be treated by a surgeon capable of performing eye surgery treatment measures.

SUMMARY OF THE INVENTION

The invention is based on the object of improving upon a generic ocular treatment device with a radiation source that emits UV light and an optical imaging system situated downstream from the radiation source, for imaging a therapy beam emitted by the radiation source in an ocular imaging plane, with an optical condenser unit situated downstream from the radiation source, a diaphragm unit, an optical means for influencing a spatial energy distribution that is assigned to the therapy beam and is oriented along the therapy beam cross section, as well as with an optical means for influencing a beam shape that can be assigned to the therapy beam, such that the cost of implementing the treatment device can be reduced significantly without having any disadvantages with regard to the beam properties of the therapy beam imaged in the ocular imaging plane. Instead, the operating friendliness of the treatment device for the treating ophthalmologist is to be improved and the therapeutically effective beam properties are to be optimized as much as possible to the geometry of the patient's eye to be treated.

The ocular treatment device according to the invention is characterized by the agent for influencing the energy distribution that can be attributed to the therapy beam is a diaphragm which is produced by an etching technique. The etched diaphragm is an inexpensive component to manufacture. A graticule, which is a transparent plate having at least one line grid printed on at least one side with the at least one line being opaque for the UV light of the radiation source, is also a suitable alternative to an etching diaphragm.

Furthermore, the optical device for influencing the beam form of the therapy beam is designed with at least one aspherical optical lens, by which the therapy beam is sharply imaged onto the spatially curved shape of the cornea of a patient's eye to be treated. That is, the ocular imaging plane assumes the shape of a curved focal surface, which is preferably adapted to the natural curvature of the eye. For this reason, the term "ocular imaging plane" is understood in the following text to refer to a spatially curved focal surface, along which the multiple beam focus points, comprising a beam cross section imaged on the ocular imaging plane, are focused.

For the purposes of facilitating and, at the same time, accurate positioning of the ocular treatment device with respect to a patient's eye to be treated, that is, for the purpose of centering as well as focusing the therapy beam in relation to an eye that has been fixed spatially and is to be treated, at least three spatially separate target beams of light are arranged spatially around the therapy beam directed at the ocular imaging plane. A stenopeic, which is a pinhole diaphragm, is introduced along each of the individual beam paths, so that the diaphragm hole is imageable through an optical imaging unit in the ocular imaging plane, so that at least three target beams of light imaged in the ocular imaging plane are equally distributed on a circular line, by which the diameter of the circle is between 3 and 15 millimeters, preferably between 5 and 8 millimeters, especially preferably 6 millimeters. The wavelength of the individual target beams of light is selected, so that an ophthalmologist performing the treatment is capable of recognizing the reflected images created on the surface of the cornea by the target beams of light with the highest possible contrast, so that these serve as precise adjustment aids for the ophthalmologist. The therapy beam whose wavelength in the ultraviolet spectral range remains invisible to the ophthalmologist is correctly adjusted and/or positioned with respect to the eye to be treated as soon as the diaphragm holes of the target beams of light are imaged sharply and concentrically around the pupil of the eye to be treated.

Furthermore, care must be taken to ensure that the direction of viewing of the patient's eye to be treated remains unchanged as much as possible during the examination. Therefore, a fixation beam is additionally arranged as an adjustment aid for the patient along the therapy beam, which is directed at the ocular imaging plane, such that a stenopeic diaphragm, whose diaphragm hole can be imaged sharply by means of an imaging lens in an imaging plane located downstream from the ocular imaging plane in the direction of the beam. The imaging lens to be provided here should be selected in a suitable manner, so that the image of the diaphragm hole along the fixation beam of light is seen sharply by the eye of the patient to be treated. Consequently, the diaphragm hole is thus to be imaged sharply on the retina of the patient's eye to be treated. In a preferred embodiment, the at least one aspherical optical lens itself serves as the imaging lens, which images the fixation beam of light and with which the beam shape of the therapy beam is adapted to the curvature of the eye to treated and is imaged sharply optically.

Due to the use of a diaphragm, which can be manufactured by means of an inexpensive etching technique and which has a diaphragm region that is permeable for the therapy beam, the number, shape and size of which can be preselected as desired, depending on the desired energy distribution along the therapy beam cross section, provides an extremely inexpensive component, which can be used as a replaceable insertion module in the beam path of the therapy beam and can be kept on hand in different embodiments in the manner of a modular principle, so that the treatment device can be adapted individually to patient-specific treatment needs.

Instead of the etching plate, a graticule with a suitably designed line pattern may be used to the same extent so that its pattern lines forms extremely fine structures.

In the same way, the at least one aspherical optical lens for beam shaping of the therapy beam that can be imaged on the ocular image plane constitutes an inexpensive measure which sharply images the therapy beam, which is predetermined individually in its energy distribution, on the spatially curved ocular imaging plane and which is adapted to the surface shape of the eye, namely, the ocular focal surface. Significant cost reductions can be achieved through the two measures mentioned above.

By additionally providing at least three target light beams arranged separately in space around the therapy beam directed at the ocular image plane as well as the fixation light beam running along the therapy beam, the handling of the treatment device designed according to the invention can be improved significantly for the ophthalmologist for the purpose of accurate adjustment of the treatment device in relation to the eye to be treated. Due to the positioning of the treatment device that can be performed by the ophthalmologist with respect to the eye to be treated, independently of the visual impression of the patient to be treated, no communication is necessary between the patient and ophthalmologist, so that the treatment of patients who speak a foreign language or patients who are unable to speak or can no longer speak, for example, babies, small children or animals, is possible without a no problem.

BRIEF DESCRIPTION OF THE DRAWINGS

The invention is described below on the basis of exemplary embodiments with reference to the drawings as examples, without restricting the general inventive idea, in which:

FIGS. 3*a, b, c, d* show alternative embodiments for implementation of an etching diaphragm and a graticule.

DETAILED DESCRIPTION OF THE INVENTION

Figure 1:
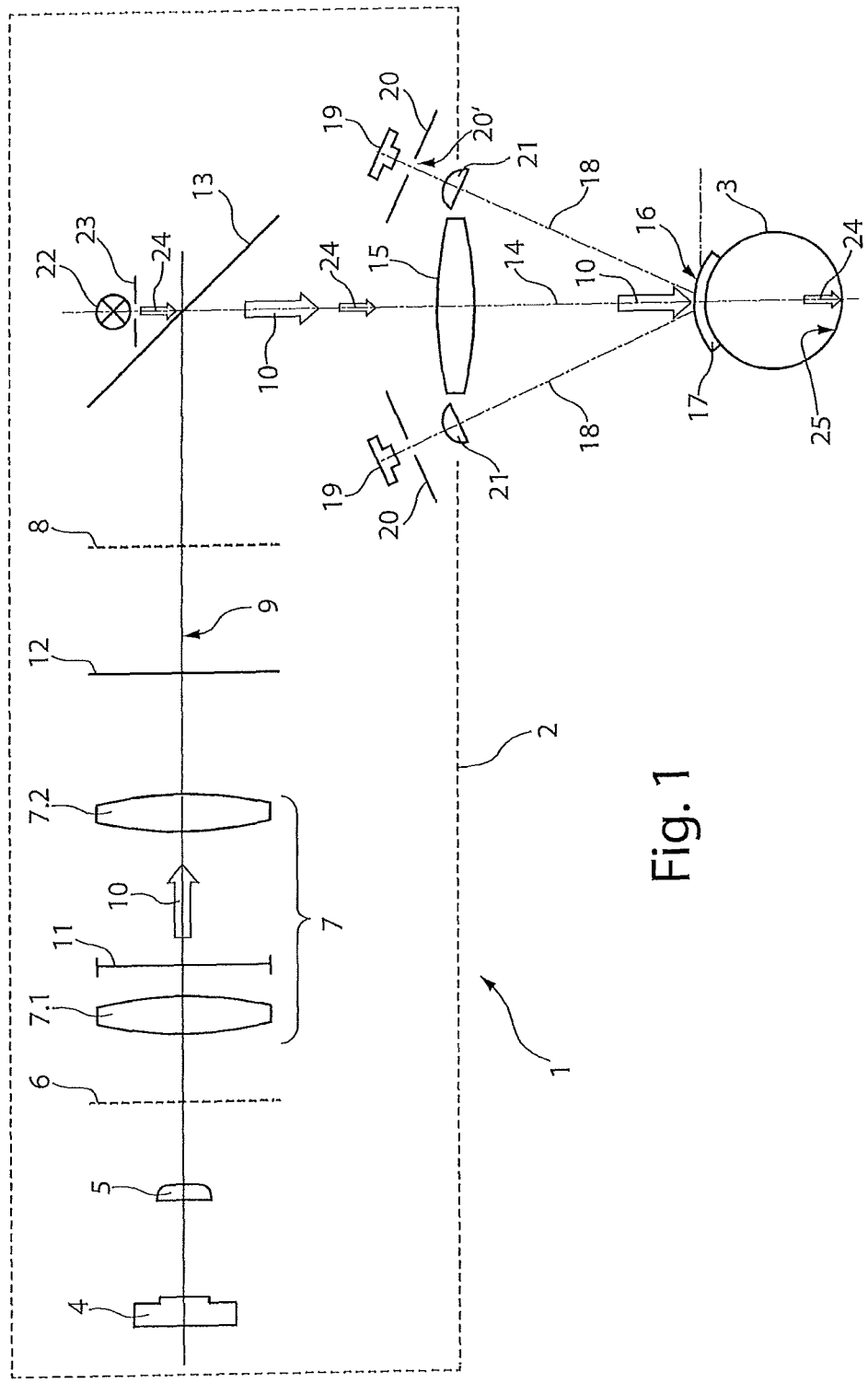
FIG. 1 shows a schematic diagram of the beam path and the optical components required for this for implementing the treatment device designed according to the invention, FIGS. 2*a, b* show detailed diagrams illustrating the components for implementation of the target light beams.

FIG. 1 shows in a schematic diagram the component design of a treatment device 1 designed according to the invention which is integrated into a housing 2 that can be handled manually and is to be positioned opposite an eye 3 that is to be treated. The treatment device 1 comprises a beam source 4, which emits UV radiation. LED light sources or lasers are preferably suitable. The UV light emitted from the radiation source 4 is bundled by a condenser unit 5 for homogeneous illumination of a first intermediate image plane 6 and is imaged therein, while the illumination optical system 7, comprised of two lenses 7.1 and 7.2, is imaged in a second intermediate image plane 8. For lateral spatial limitation of the therapy beam 10 propagating along the first optical axis 9 defined by the illumination lens, an iris diaphragm 11 mounted directly after the first lens 7.1 of the illumination optical system 7 and whose diaphragm diameter is adjustable variably can be used for this spatial limitation. The choice of the diaphragm diameter can be made as a function of the respective therapeutically active beam diameter size required at the site of the eye to be treated with the help of a suitably designed adjusting unit.

Furthermore, an etching diaphragm 12 is situated outside of the second intermediate image plane 8 situated downstream from the beam path along the first optical axis 9 of the illumination optical system 7; its extensive distribution of the diaphragm regions that are permeable for the therapy beam 10 as well as their shape and size make it possible to predefine the energy distribution of the therapy beam 10 along its therapy beam cross section in a suitable manner. Details regarding the possible design of such an etching diaphragm are also given below with reference to FIG. 3. Instead of the etching diaphragm 12, a graticule 33 can also be used, and reference is made to FIG. 3d for its possible design.

Figure 5:
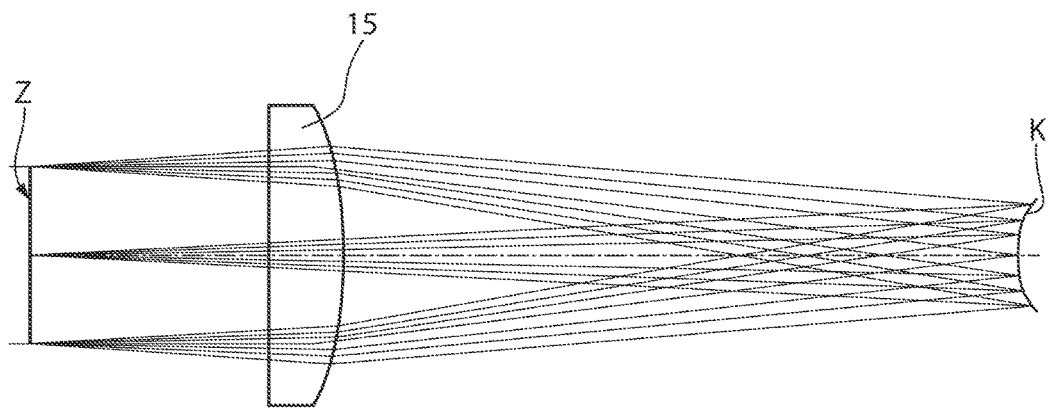
FIG. 5 shows a comparison of the beam path between an optical lens with and without the asphericity.

An optical deflecting unit 13 which is mounted in the beam path of the therapy beam 10 and which is preferably designed as a dividing mirror ensures a deflection of the therapy beam 10, preferably oriented by 90° out of the first optical axis 9 into a second optical axis 14, along which an aspherical lens 15 is mounted downstream from the deflecting unit 13. The aspherical lens 15 is arranged and designed in such a way that it sharply focuses the therapy beam 10 on an ocular imaging plane 16, wherein the ocular imaging plane 16 corresponds to a curved focal surface that corresponds to the curved surface 17 of the cornea of the eye 3 to be treated. Due to the aspherical lens 15, the beam profile of the therapy beam 10 striking the eye to be treated is shaped, so that the therapy beam 10 is imaged in its entire cross-sectional area with precise focusing on the naturally curved corneal surface. To illustrate this beam shaping, reference is made here to FIG. 5, in which the circular line K corresponds to the naturally curved corneal surface 17. Due to the aspherical lens 15, the focal plane of the optical image is deformed exactly along the curved corneal surface 17, so that a sharp image of the therapy beam 10 on the entire corneal surface is ensured (see FIG. 5). In this case, an aspherical lens 15 sharply images a beam, which is imaged in an intermediate image plain Z, on a curved focal plane, which corresponds to the ocular "curved" imaging plane 16 in the case of the subject matter of the present invention. It can be seen clearly that the plurality of beam focus points comprising the beam focus in its entire lateral beam cross-sectional extent lie along the focal surface K, which has a circular curvature.

In addition, the treatment device 1 according to the invention provides three target beams of light 18, arranged so that they are equally distributed around the second optical axis 14, but FIG. 1 shows only two of these target beams of light for illustration purposes. The target beams make it easier for the treating ophthalmologist to accurately position the treatment device 1 in relation to a patient's eye 3 that is to be treated and is fixed in spatial position.

A light source 19 as shown in FIG. 1 is used to generate each of the at least three target light beams 18, its wavelength being in the visible spectral range and being selected, so that it is manifested in reflection on the iris with the greatest possible contrast. A stenopeic diaphragm 20, which typically has a circular diaphragm hole 20', typically with a hole diameter of 0.5 to 2 mm, is situated in the beam path of each individual target beam 18 directed at the eye 3. The diaphragm hole 20' is also imaged sharply on the iris by means of an optical imaging unit 21 and preferably also is an aspherical lens, so that the at least three target light beams 18 imaged in the ocular imaging plane 16 are situated in an equal distribution on a circular line, in which the diameter of the circle is measured as being between 3 and 15 millimeters, preferably 5 to 8 millimeters, especially preferably 6 millimeters, wherein the midpoint of the circle of the geometric center of the therapy beam 10, which is imaged sharply in the ocular image plane, corresponds to the geometric center. Additional details will be explained below with FIG. 2 in this context.

Furthermore, the treatment device 1 according to the invention has another light source 22, whose light is also in the visible spectral range, which clearly differs in wavelength from the target light beams 18, to provide a different color impression. The light source 22 is arranged on the back of the optical deflecting unit 13. The optical deflecting unit 13 is preferably a partially transparent mirror, which deflects the therapy beam 10 with the lowest possible loss, on the one hand, but, on the other hand, the light emitted by the light source 22 passes through the mirror with almost no loss. A stenopeic diaphragm 23, which shapes a fixation light beam 24 which additionally passes through the aspherical lens 15 along the second optical axis 14, is situated directly downstream from the light source 22. The fixation light beam 24 is directed by the aspherical lens at the eye in such a way that the fixation light beam is imaged sharply on the retina 25 of the eye 3 to be treated. The fixation light beam 24 helps the patient in particular to leave the direction of view of the eye 3 to be treated unchanged during the therapeutic measure.

Figures 2A, 2B:
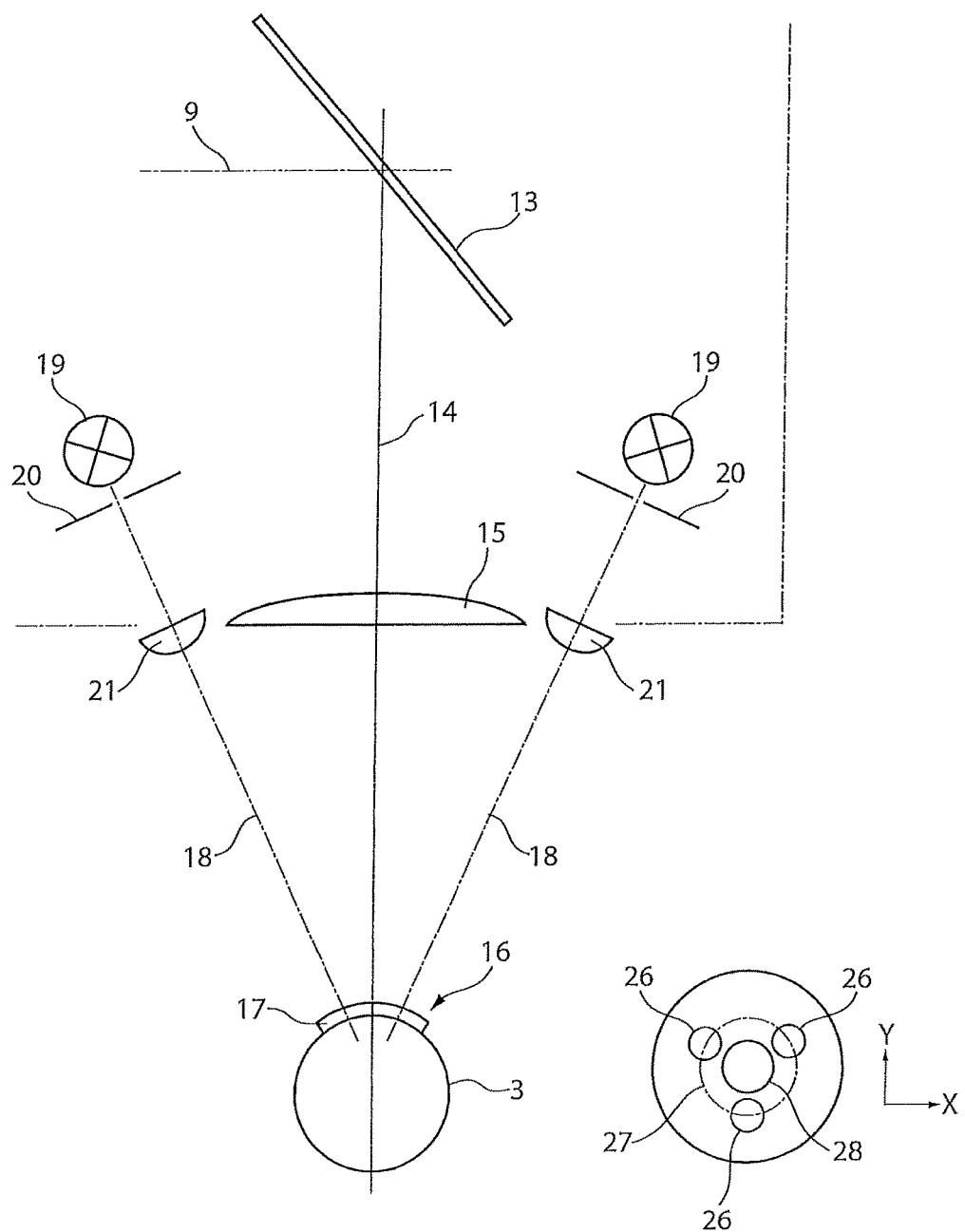

FIG. 2a shows an enlarged schematic side view of the optical design for generating the target light beams 18. Of the at least three target light beams 18, FIG. 2a shows two target light beams 18, an LED light source 19, which is mounted inside the treatment device 1 and generates the target light beams. The LED light source 19 emits light in the visible spectral range, preferably green light which passes through a stenopeic diaphragm 20, which is situated in the immediate vicinity of the light source 19 and has a diaphragm hole 20' with a hole diameter of preferably 1 mm. The target light beam 18 passing through the stenopeic diaphragm 20 subsequently goes to an optical imaging unit 21, which is designed as an aspherical lens that images the diaphragm hole 20' sharply in the ocular imaging plane 16.

The aspherical lenses 21 assigned to the respective beam paths of the at least three target light beams 18 are arranged in an equal distribution around and directly next to the aspherical lens 15, which serves to image the therapy beam 10 on the ocular imaging plane 16. Thus, the images of the diaphragm holes 20' are distributed uniformly in the ocular imaging plane 16 along a circular line, whose circle diameter is typically 6 mm. the diaphragm hole images 26 along the circular line 27 are illustrated in FIG. 2b. As soon as an ophthalmologist to be performing the treatment has adjusted the device with respect to the eye 3 to be treated such that the reflection pattern illustrated in FIG. 2b is obtained on the surface of the eye, i.e., the reflected images 26 of the diaphragm holes 20' are arranged concentrically with the pupil 28 of the eye 3 to be treated, the concentricity of the therapy beam 10 in the x direction relative to the eye is then ensured. As soon as the treating physician can perceive all three reflected images 26 sharply on the iris of the eye 3 to be treated, this also ensures that the correct distance between the treatment device 1 and the eye 3 has been set.

FIGS. 3a, b and c show different embodiments of etching diaphragms 12, each of which has diaphragm regions 29 which are permeated by the therapy beam 10, each being surrounded by a diaphragm region 30 that remains opaque for to the therapy beam 10. The spatial distribution and the design of the shape and size of the plurality of individual diaphragm regions 29 which are permeated by the therapy beam can basically be selected as desired and are to be selected according to the type and properties of the respective eye to be treated. For example, if an energy distribution is to be created along the beam cross section of the therapy beam, corresponding to the energy profile illustrated in FIG. 3a, which is largely characterized by a rectangular energy profile with a central dip in the energy distribution, then the diaphragm regions 29 that are permeable for the therapy beam are to be designed in the size and shape according to the etching diaphragm 12 illustrated in FIG. 3a. The permeable diaphragm regions 29 may be circular, elliptical, rectangular, segmented or basically one-piece cohesive surface regions of any desired shape. FIG. 3b shows the permeable diaphragm regions 29 as segmented surface shapes; FIG. 3c shows an exemplary embodiment having an asymmetrical energy distribution along the beam cross section, especially since the largest permeable diaphragm region 29 is positioned excentrically with respect to the geometric midpoint M of the etching diaphragm 12. Furthermore, several smaller diaphragm regions are arranged excentrically and asymmetrically in relation to the midpoint M of the diaphragm. FIG. 3d shows a graticule 33, which has a line grid located centrally with a plurality of intersecting lines that define plate regions that are opaque to passage of the therapy beam. The therapy beam is diminished in intensity in the region of the line grid, so that the therapy beam passing through the graticule 33 undergoes a weakening in intensity at the center of the beam, whereas the beam passing through in the region of the permeable plate regions 34 does not experience any weakening.

Figure 4:
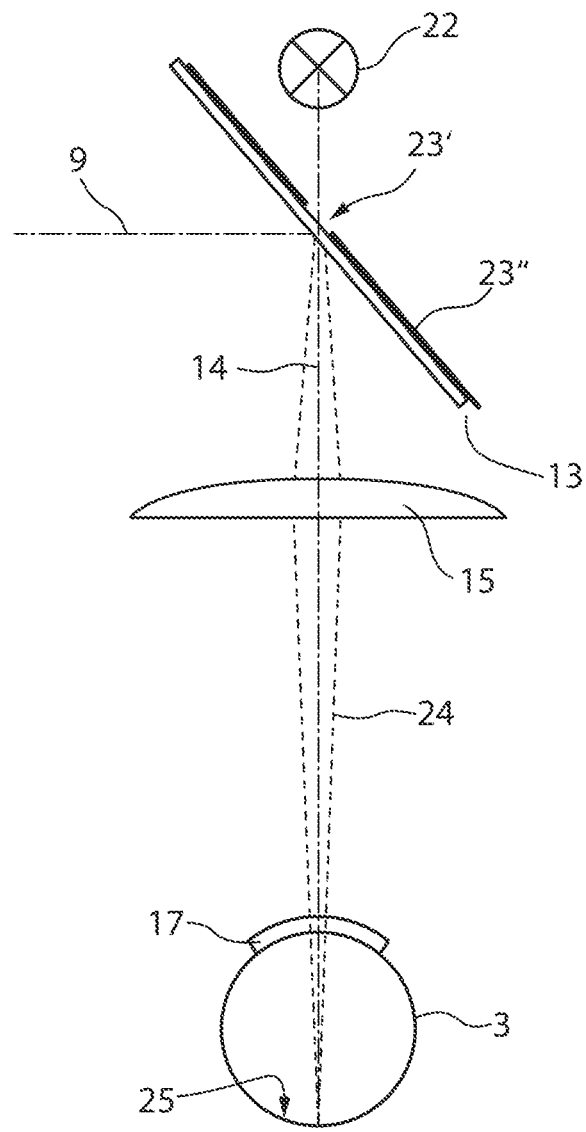
FIG. 4 shows a detailed diagram illustrating the creation and imaging of the fixation beam of light on the retina of an eye to be treated.

FIG. 4 shows a detailed diagram for creating the fixation beam of light 24, which is used for the patient to be treated. It is desirable to hold the eye 3 that is to be treated with the therapy beam as immovably and as accurately as possible to be aligned with the fixation beam of light 24 during the treatment. To this end, an LED light source 22, which emits light in the visible spectral range, is positioned on the back, facing the optical deflection unit 13. The optical deflection unit 13 is fundamentally designed as a full mirror for the therapy beam, which is not shown in FIG. 4. The optical deflection unity 13 has an optical distributor function, at least in the central region making it possible for light of the LED light source 22 to pass through the optical deflecting unit 13 during transmission. There is a stenopeic diaphragm with a diaphragm opening 23' having a hole diameter of approximately 1 mm situated on the back with respect to the deflecting unit 13, allowing the fixation beam to pass sharply in the direction of the second optical axis. The stenopeic diaphragm 23 may be implemented in the form of a material layer 23" applied to the deflecting unit 13 at the back, this material layer being opaque for the light emitted by the LED light source 22, except for the diaphragm opening. The aspherical lens 15, which then follows in the beam path, images the diaphragm opening 23' sharply on the retina 25 of the eye 3 when combined with the optical imaging properties of the eye itself.

Figure 6:
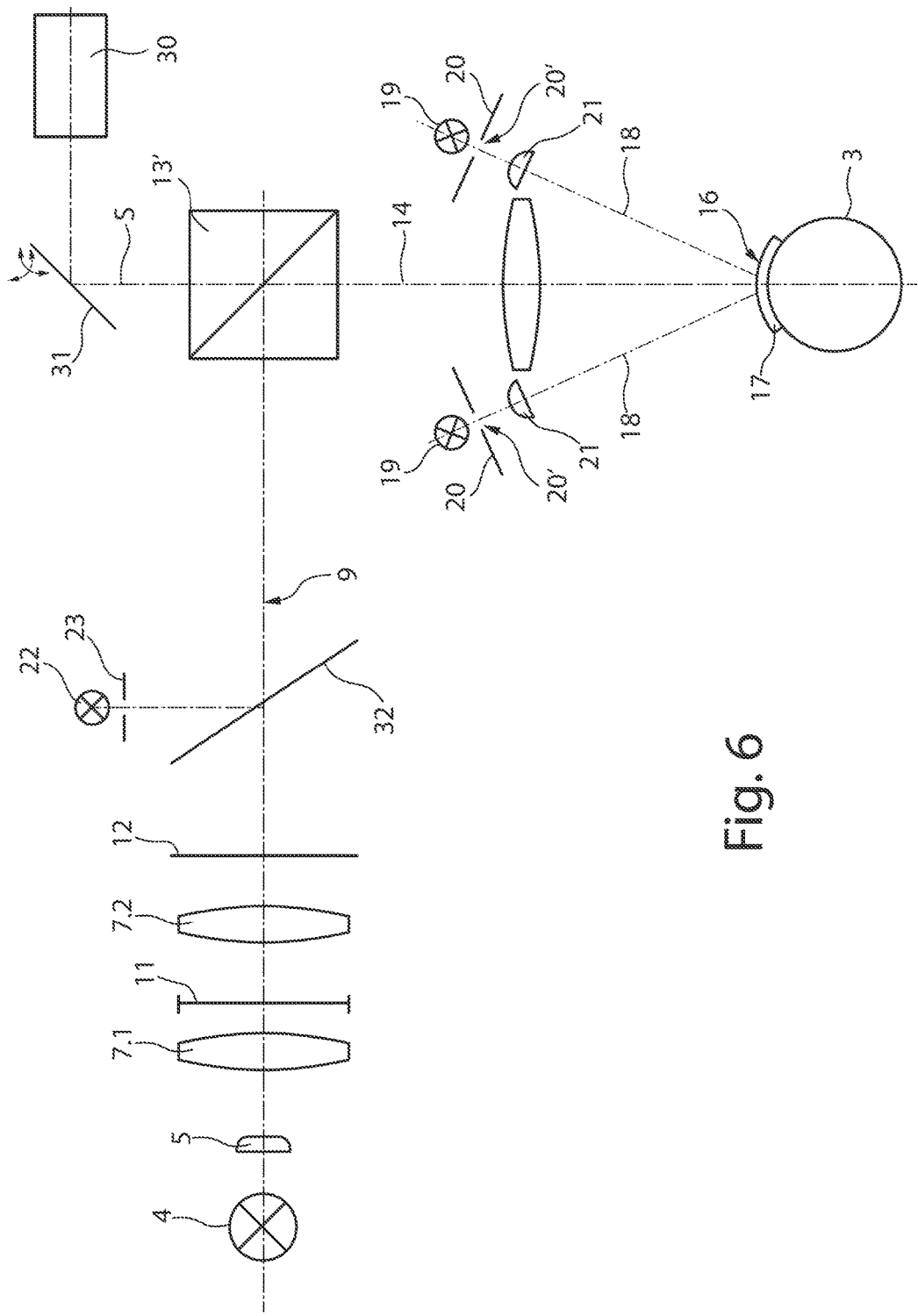
FIG. 6 shows a schematic diagram of a component display for a treatment device designed according to the invention, with input of another beam path, for example, for examining the ocular fundus.

FIG. 6 shows an alternative embodiment for implementation of the treatment device according to the invention, with which it is possible to input another beam path, in addition to the therapy beam 10 and the fixation beam of light 24, along the second optical axis 14, with which the beam path of other diagnostic devices, for example, can be input for examination of the eye. To avoid repeated explanation of components that have been described already, the components shown in FIG. 6 are labeled with the same reference numerals already introduced and explained above. In contrast with the instrument design illustrated in FIG. 1 which uses a deflecting mirror, a distributor mirror or a prismatic distributor cube 13' is used which is capable of deflecting the therapy beam 10 in the same way out of the first optical axis 9 and into the second optical axis 14, on the one hand, but is capable of inputting another beam path S along the second optical axis 14 for the eye examination, on the other hand. The additional beam path S thus originates, for example, from an arrangement for carrying out an optical coherence tomography, abbreviated as OCT 30, whose illumination and observation beam paths are deflected by means of a scanner optical system 31 that deflects the beam path S for examination of the ocular fundus.

The fixation beam of light 24, which serves to control the direction of view for the patient to be treated, is input by means of a distributor mirror 32, which inputs the fixation light beam 24 at first along the first optical axis 9 superimposed on the therapy beam 10, which is directed onto the eye to be examined jointly with the therapy beam 10 within the distributor cube 13' in the direction of the second optical axis 14.

LIST OF REFERENCE NUMERALS

1 treatment device
2 housing
3 eye
4 beam radiation source
5 condenser unit
6 first intermediate image plane
7 illumination optical system
7.1 lens
7.2 lens
8 second intermediate image plane
9 first optical axis
10 therapy beam
11 iris diaphragm
12 etching diaphragm
13 optical deflecting unit
13' distributor cube
14 second optical axis
15 aspherical lens
16 ocular imaging plane
17 corneal surface
18 target light beam
20 stenopeic diaphragm
20' diaphragm hole
21 optical imaging unit, aspherical lens
22 light source
23 stenopeic diaphragm
23' diaphragm opening
23" material layer with diaphragm opening
24 fixation light beam
25 retina
26 reflected image of the diaphragm hole 20'
27 circular line
28 pupil
30 ophthalmoscope
31 scanner optical system
32 distributor mirror
33 graticule
34 transparent regions of the graticule
35 opaque regions of the graticule

The invention claimed is:
1. An ocular treatment device comprising:
a radiation source which emits UV light;
an optical imaging system located downstream from the radiation source for imaging a therapy beam emitted by the radiation source on an ocular imaging plane;

an optical condenser downstream from the radiation source, an illumination optical system including at least two optical lenses and at least one aspherical optical lense;

a diaphragm;

an optical means for influencing a spatial energy distribution of the therapy beam oriented along a cross section of the therapy beam including either an etched diaphragm or a printed graticule;

an optical means for influencing shape of the therapy beam which includes at least one aspherical optical lens;

at least three spatially separated target light beams disposed on a circular line spatially around the therapy beam and directed at the ocular imaging plane;

a stenopeic diaphragm disposed along each of the separated target light beams and including a diaphragm hole which is imageable in the ocular imaging plane by an imaging optics, so that the at least three separated target light beams are imaged in the ocular imaging plane and are located on a circular line having a diameter between 3 and 15 mm;

a fixation light beam oriented at the ocular imaging plane which is disposed along the therapy beam and is directed at the ocular imaging plane; and another stenopeic diaphragm disposed along the fixation light beam including a diaphragm hole which is imaged on the imaging optics disposed along the therapy beam in an imaging plane downstream from the ocular imaging plane.

2. The treatment device according to claim 1, wherein the optical imaging system comprises:

the optical condenser imaging the therapy beam along a first optical axis in a first intermediate image plane;

the illumination optical system including the at least two optical lenses which image the first intermediate image plane on a second intermediate image plane;

the at least one aspherical optical lens which images the second intermediate image plane in the ocular imaging plane; and an optical deflector disposed between the illumination optical system and the at least one aspherical optical lens which deflects the therapy beam along the first optical axis into a second optical axis directed at the ocular imaging plane.

3. The treatment device according to claim 2, comprising:

an iris diaphragm disposed between the at least two optical lenses of the illumination optical system; and an etched diaphragm or a printed graticule disposed between the illumination optical system and the at least one aspherical optical lens which is outside of the second intermediate image plane.

4. The treatment device according to claim 3, wherein:

an iris diaphragm disposed between the at least two optical lenses of the illumination optical system; and an etched diaphragm or a printed graticule disposed between the illumination optical system and the at least one aspherical optical lens which is outside of the second intermediate image plane.

5. The treatment device according to claim 4, comprising:

a light source which generates one of the at least three separated target light beams; and wherein the optical imaging system includes an aspherical lens.

6. The treatment device according to claim 5, wherein:

the at least three separated target light beams each have an optical axis; and the light source, the stenopeic diaphragm and the aspherical lens are disposed along an optical axis of the three separated target light beams.

7. The treatment device according to claim 3, wherein:

the printed graticule includes plate regions which are permeable to the therapy beam with each plate permeable region being surrounded at least partially by a plate region that is opaque to passage of the therapy beam;

each of the permeable plate regions is divided into at least two groups in which the permeable plate regions differ in at least one of shape and size; and the opaque plate regions are printed.

8. The treatment device according to claim 7, comprising:

a light source which generates one of the at least three separated target light beams; and wherein the optical imaging system includes an aspherical lens.

9. The treatment device according to claim 8, wherein:

the at least three separated target light beams each have an optical axis; and the light source, the stenopeic diaphragm and the aspherical lens are disposed along an optical axis of the three separated target light beams.

10. The treatment device to claim 8, wherein:

the at least three separated target light beams each have an optical axis; and the light source, the stenopeic diaphragm and the aspherical lens are disposed along an optical axis of the three separated target light beams.

11. The treatment device according to claim 3, comprising:

a light source which generates one of the at least three separated target light beams; and wherein the optical imaging system includes an aspherical lens.

12. The treatment device according to claim 11, wherein:

the at least three separated target light beams each have an optical axis; and the light source, the stenopeic diaphragm and the aspherical lens are disposed along an optical axis of the three separated target light beams.

13. The treatment device according to claim 2, comprising:

a light source which generates one of the at least three separated target light beams; and wherein the optical imaging system includes an aspherical lens.

14. The treatment device according to claim 2, wherein:

the optical means for influencing shape of the therapy beam includes imaging optics which images a fixation light beam on an imaging plane downstream from the ocular imaging plane.

15. The treatment device according to claim 2, wherein:

the optical deflector reflects the therapy beam and transmits the fixation light beam; and comprises a light source for generating the fixation light beam and a stenopeic diaphragm disposed along the second optical axis and disposed opposite to the at least one aspherical optical lens relative to the optical deflector.

16. The treatment device according to claim 1, comprising:

a light source which generates one of the at least three separated target light beams; and wherein the optical imaging system includes an aspherical lens.

17. The treatment device to claim 16, wherein:

a light source which generates one of the at least three separated target light beams; and wherein the optical imaging system includes an aspherical lens.

18. The treatment device according to claim 1, wherein:

the optical means for influencing the shape of the therapy beam includes imaging optics which images the fixation light beam on an imaging plane downstream from the ocular imaging plane.

* * * * *